United States Patent [19]

Wnuk et al.

[11] Patent Number: 5,391,423
[45] Date of Patent: Feb. 21, 1995

[54] BIODEGRADABLE, LIQUID IMPERVIOUS MULTILAYER FILM COMPOSITIONS

[75] Inventors: Andrew J. Wnuk, Wyoming; Thurman J. Koger, II, Hamilton; Terrill A. Young, Cincinnati, all of Ohio

[73] Assignee: The Procter & Gamble Company, Cincinnati, Ohio

[21] Appl. No.: 126,672

[22] Filed: Sep. 24, 1993

Related U.S. Application Data

[63] Continuation of Ser. No. 905,057, Jun. 26, 1992, abandoned.

[51] Int. Cl.6 .................. B32B 7/02; B32B 27/36; B32B 27/00
[52] U.S. Cl. .................. 428/217; 428/220; 428/424.8; 428/425.1; 428/532; 428/500; 428/480; 428/913
[58] Field of Search ........... 428/500, 480, 532, 217, 428/220, 425.1, 424.8, 913

[56] References Cited

U.S. PATENT DOCUMENTS

| | | |
|---|---|---|
| 3,814,101 | 6/1974 | Kozak . |
| 3,867,324 | 2/1975 | Clendinning et al. . |
| 3,901,838 | 8/1975 | Clendinning et al. . |
| 3,922,239 | 11/1975 | Koleske et al. . |
| 3,925,504 | 12/1975 | Koleske et al. . |
| 3,931,068 | 1/1976 | Clendinning et al. . |
| 3,949,145 | 4/1976 | Otey et al. . |
| 3,952,347 | 4/1976 | Comerford et al. . |
| 4,002,171 | 1/1977 | Taft . |
| 4,011,871 | 3/1977 | Taft . |
| 4,016,117 | 4/1977 | Griffin . |
| 4,021,388 | 5/1977 | Griffin . |
| 4,047,862 | 9/1977 | Keith . |
| 4,051,306 | 9/1977 | Tobias et al. . |
| 4,133,784 | 1/1979 | Otey et al. . |
| 4,284,671 | 8/1981 | Cancio et al. . |
| 4,337,181 | 6/1982 | Otey et al. . |
| 4,372,311 | 2/1983 | Potts . |
| 4,454,268 | 6/1984 | Otey et al. . |
| 4,503,098 | 3/1985 | Potts . |
| 4,673,438 | 3/1986 | Wittwer et al. . |
| 4,745,160 | 5/1988 | Churchill . |
| 4,826,493 | 5/1989 | Martini et al. . |
| 4,873,270 | 10/1989 | Aime et al. . |
| 4,880,592 | 11/1989 | Martini et al. . |
| 4,915,893 | 4/1990 | Gogolewski et al. . |
| 4,916,193 | 4/1990 | Tang et al. . |
| 4,962,164 | 10/1990 | Jabarin et al. . |
| 4,964,857 | 10/1990 | Osborn . |
| 4,983,651 | 1/1991 | Griffin . |
| 5,026,363 | 6/1991 | Pratt . |
| 5,026,589 | 6/1991 | Schechtman . |
| 5,037,410 | 8/1991 | Zimmerman et al. . |
| 5,053,482 | 10/1991 | Tietz . |
| 5,095,054 | 3/1992 | Lay et al. . |
| 5,097,004 | 3/1992 | Gallagher et al. . |
| 5,097,005 | 3/1992 | Tietz . |
| 5,110,852 | 5/1992 | Gogolewski et al. . |
| 5,114,537 | 5/1992 | Scott et al. . |
| 5,166,232 | 11/1992 | Muller et al. . |
| 5,171,308 | 12/1992 | Gallagher et al. . |
| 5,171,309 | 12/1992 | Gallagher et al. . |
| 5,171,640 | 12/1992 | Wirth . |
| 5,185,009 | 2/1993 | Sitnam . |
| 5,190,533 | 3/1993 | Blackburn . |
| 5,191,734 | 3/1993 | Weber et al. . |
| 5,196,247 | 3/1993 | Wu et al. . |
| 5,217,795 | 6/1993 | Sasse et al. . |
| 5,217,803 | 6/1993 | McBride et al. . |

FOREIGN PATENT DOCUMENTS

| | | |
|---|---|---|
| 0226439A1 | 6/1987 | European Pat. Off. . |
| 0326517A1 | 8/1989 | European Pat. Off. . |
| 0327505A2 | 8/1989 | European Pat. Off. . |
| 89810373.4 | 11/1989 | European Pat. Off. . |

(List continued on next page.)

OTHER PUBLICATIONS

Derwent Publications Ltd., AN 92-402561 (JP,A,4 299 131; Dainippon Printing Co. Ltd), Oct. 22, 1992.
Derwent Publications Ltd., AN 93-120862 (JP,A,5 057 833; JSP Corp.), Mar. 9, 1993.
Derwent Publications Ltd., AN 93-263106 (JP,A,4 178 466; Shingijutsu Kaihatsu Jigyodan), Jun. 25, 1992 with English language translation of JP,A,4-178-466.
Derwent Publications Ltd., AN 92-155471 (JP,A,4 093

(List continued on next page.)

*Primary Examiner*—P. C. Sluby
*Attorney, Agent, or Firm*—Bart S. Hersko; Loretta J. Henderson; E. Kelly Linman

[57] ABSTRACT

Biodegradable, liquid impervious multilayer film compositions are disclosed. In particular, the films comprise composite structures derived from multilayer combinations of biodegradable polymers. The biodegradable polymers are selected from the categories of moisture sensitive polymers, thermally sensitive polymers, mechanically limited polymers, polymers not easily processed into films, hydrolytically cleavable polymers, and degradable elastomers. Optionally, the multilayer films may further comprise additional adhesive tie layers. The biodegradable polymers are combined in various ways to overcome the deficiencies of the individual components, yet at the same time impart specific performance properties to the film. The multilayer film compositions are suitable for use as backsheets in disposable absorbent products including diapers, adult incontinent pads, sanitary napkins, pantiliners, and the like.

11 Claims, No Drawings

FOREIGN PATENT DOCUMENTS

| | | |
|---|---|---|
| 0400531A1 | 12/1990 | European Pat. Off. . |
| 0400532A1 | 12/1990 | European Pat. Off. . |
| 0408503A2 | 1/1991 | European Pat. Off. . |
| 0409781A2 | 1/1991 | European Pat. Off. . |
| 0409782A2 | 1/1991 | European Pat. Off. . |
| 0435435A2 | 7/1991 | European Pat. Off. . |
| 0450777A2 | 10/1991 | European Pat. Off. . |
| 91103879.2 | 10/1991 | European Pat. Off. . |
| 91106627.2 | 10/1991 | European Pat. Off. . |
| 0512360A1 | 11/1992 | European Pat. Off. . |
| 0525245A1 | 2/1993 | European Pat. Off. . |
| 0533144A2 | 3/1993 | European Pat. Off. . |
| 4016348A1 | 5/1990 | Germany . |
| 4110455C1 | 6/1991 | Germany . |
| 2243327A | 10/1991 | United Kingdom . |
| WO90/10671 | 9/1990 | WIPO . |
| WO91/02023 | 2/1991 | WIPO . |
| WO91/02024 | 2/1991 | WIPO . |
| WO91/02025 | 2/1991 | WIPO . |
| WO91/08726 | 6/1991 | WIPO . |
| WO91/13207 | 9/1991 | WIPO . |
| WO92/01733 | 2/1992 | WIPO . |
| WO92/04410 | 3/1992 | WIPO . |
| WO92/09654 | 6/1992 | WIPO . |
| WO92/15454 | 9/1992 | WIPO . |
| WO92/19680 | 11/1992 | WIPO . |
| WO93/00116 | 1/1993 | WIPO . |
| WO93/00399 | 1/1993 | WIPO . |
| WO93/03098 | 2/1993 | WIPO . |

OTHER PUBLICATIONS

315; Denki Kagaku Kogyo), Mar. 26, 1992 with English language translation of JP,A,4-093-315.

The Prospects for Biodegradable Plastics, F. Rodriguez, CHEM TECH, Jul. 1971, pp. 409-415.

Derwent Publications Ltd., abstract No. 90-31532-2/A2, JO 2222-421-A (Japan).

Influence of Copolymer Structure on Properties of Poly-$\beta$-Hydroxyalkanoates; Marchessault et al.; Polym. Mater. Sci. Eng. 62 pp. 226-230, (1990).

BIODEGRADABLE, LIQUID IMPERVIOUS MULTILAYER FILM COMPOSITIONS

This is a continuation of application Ser. No. 07/905,057, filed on Jun. 26, 1992, now abandoned.

TECHNICAL FIELD

The present invention relates to liquid impervious films comprising multilayer structures of biodegradable thermoplastic polymers. The films are especially suitable for use as backsheets in articles such as diapers, sanitary napkins, pantiliners, and the like, which are adapted for absorbing various bodily fluids. The films herein may also be used in a sealable packaging film, plastic garbage bags, etc.

BACKGROUND OF THE INVENTION

A wide variety of absorbent articles designed to be efficient for the absorption of body fluids such as blood, urine, menses, and the like, are known. Disposable products of this type generally comprise some sort of fluid-permeable topsheet material, an absorbent core, and a fluid-impermeable backsheet material. Heretofore, such absorbent structures have been prepared using, for example, topsheet materials prepared from woven, non-woven, or porous formed-film polyethylene or polypropylene materials. Backsheet materials typically comprise flexible polyethylene sheets. Absorbent core materials typically comprise wood pulp fibers or wood pulp fibers in combination with absorbent gelling materials. One aspect of such absorbent articles that has recently been considered is their disposability. Although such products largely comprise materials which would be expected ultimately to degrade, and although products of this type contribute only a very small percentage of the total solid waste materials generated by consumers each year, nevertheless, there is currently a perceived need to devise such disposable products from materials which are compostable.

A conventional disposable absorbent product is already to a large extent compostable. A typical disposable diaper, for example, consists of about 80% of compostable materials, e.g., wood pulp fibers, and the like. In the composting process soiled disposable absorbent articles are shredded and commingled with organic waste prior to the composting per se. After composting is complete, the non-compostable particles are screened out. In this manner even today's absorbent articles can successfully be processed in commercial composting plants.

Nevertheless, there is a need for reducing the amount of non-compostable materials in disposable absorbent articles. There is a particular need to replace polyethylene backsheets in absorbent articles with liquid impervious films of biodegradable material, because the backsheet is typically one of the largest non-compostable components of a conventional disposable absorbent article.

In addition to being biodegradable, the films employed as backsheets for absorbent articles must satisfy many other performance requirements. For example, the resins should be thermoplastic such that conventional film processing methods can be employed. These methods include cast film and blown film extrusion of single layer structures and cast or blown film coextrusion of multilayer structures. Other methods include extrusion coating of one material on one or both sides of a compostable substrate such as another film, a nonwoven fabric, or a paper web.

Still other properties are essential in product converting operations where the films are used to fabricate absorbent articles. Properties such as tensile strength, tensile modulus, tear strength, and thermal softening point determine, to a large extent, how well a film will run on converting lines.

In addition to the aforementioned properties, still other properties are needed to meet the end user requirements of the absorbent article. Film properties such as impact strength, puncture strength, and moisture transmission are important since they influence the absorbent articles durability and containment while being worn.

Once the absorbent article is disposed of and enters a composting process, other properties become important. Regardless of whether incoming waste is preshredded or not, it is important that the film or large film fragments undergo an initial breakup to much smaller particles during the initial stages of composting. Otherwise, the films or large fragments may be screened out of the compost stream and may never become part of the final compost.

During the initial stages of composting, for example where a Daneco drum is employed, the film is exposed to mechanical action, elevated temperatures, and moisture, in addition to microorganisms. Any one or two or all three of these elements can be used to promote the initial breakup of the film or large film fragments to much smaller fragments.

Many biodegradable polymers exist which are sensitive to mechanical action or elevated temperatures, or moisture. Many would individually meet the requirements for composting. However, few if any, can meet all processing, converting, end user, and disposal requirements of films suitable for backsheets of absorbent articles. To meet all these requirements simultaneously in a single film, various biodegradable polymers must be combined in ways which overcome their individual deficiencies and do not compromise the beneficial properties associated with the individual biodegradable polymers.

It is, therefore, an object of the present invention to provide liquid impervious films comprising biodegradable polymers and suitable for use in absorbent articles such as disposable diapers, catamenials, and the like. It is a particular object of the present invention to provide such films wherein the properties of the films meet the requirements outlined below:

a) a machine direction (MD) tensile modulus from about 10,000 to about 100,000 lbs./sq. in. ($6.895 \times 10^8$ dynes/sq. cm. to $6.895 \times 10^9$ dynes/sq. cm.);

b) a MD tear strength of at least 70 grams per 25.4 microns of thickness;

c) a cross machine direction (CD) tear strength of at least 70 grams per 25.4 microns of thickness;

d) an impact strength of at least 12 cm. as measured by falling ball drop;

e) a moisture transport rate less than about 0.0012 grams per square centimeter per 16 hours;

f) a modulus at 60° C. of at least $5.52 \times 10^7$ dynes/sq. cm. (800 lbs./sq. in.); and g) a thickness from about 12 microns to about 75 microns.

BACKGROUND ART

Degradable mulch films comprising starch, polyvinylalcohol, and glycerol are disclosed in U.S. Pat. No. 3,939,145, issued to Otey and Mark on Apr. 6, 1976. The degradability of the films is controlled by application of a non-degradable water resistant coating based on mixtures of polyol-toluene diisocyanate prepolymers with poly (vinylidene chloride/acrylonitrile) copolymers or poly(vinyl chloride) resins mixed with plasticizers.

Degradable mulch films with improved moisture resistance and comprising starch and ethylene/acrylic acid copolymers are disclosed in U.S. Pat. No. 4,133,784, issued to Otey and Westhoff on Jan. 9, 1979, and U.S. Pat. No. 4,337,181, issued to Otey and Westhoff on Jun. 29, 1982. The films disclosed in the latter patent also include a neutralizing agent such as ammonia, which allows them to be processed by blown film technology with good properties. Polyethylene is specified as an optional component in the films. Applications such as garbage bags and various types of packaging are also contemplated in U.S. Pat. No. 4,337,181.

International Patent Application WO90/10671, discloses biodegradable articles based on starch. In particular, destructurized starch and ethylene/acrylic acid copolymer are combined to form an interpenetrated network. It has also been disclosed that an ethylene/vinyl alcohol copolymer can be used in place of the ethylene/acrylic acid copolymer. Procedures for extruding sheets and films are also disclosed.

European Patent Application 89810373.4, discloses polymer compositions obtained from a melt comprising at least one water-containing destructurized hydrophilic polymer and at least one synthetic essentially water-insoluble thermoplastic polymer. The materials are said to be shapable under conditions of controlled water content and pressure into bottles, sheets, films, packaging materials, sacks, bags, and other articles.

U.S. Pat. No. 5,095,054, issued to Lay et al., on Mar. 10, 1992, discloses thermoplastic polymer compositions comprising a (1) destructurized starch component, (2) a second component selected from one of twelve groups of polymers bearing various types of chemically functional moieties, or (3) at least one substantially water-insoluble thermoplastic polymer. Combinations of (1), (2), and (3) are also disclosed.

A biodegradable, liquid impervious sheet laminate is described in British Patent Application GB 2,243,327 A. The laminate comprises a layer of biodegradable thermoplastic polymer, preferably copolymers of hydroxybutyric acid and other hydroxy acids, and at least one layer of a biodegradable woven or non-woven fibrous substrate, preferably a rayon non-woven fabric. The tensile strength of sheet laminates suitable for backsheets of absorbent articles such as diapers, is at least 4 Newtons, preferably at least 5 Newtons.

Disposable sanitary articles comprising biodegradable film and fiber components derived from polymers based on dioxanone are disclosed in U.S. Pat. No. 5,026,589, issued to Schechtman on Jun. 25, 1991. Also disclosed are copolymers of dioxanones with other monomers such as caprolactone, lactic acid, glycolic acid, and the like. Specific copolymer compositions providing properties essential to backsheet use are not given.

U.S. Pat. No. 4,873,270, discloses a substance based on polyurethane from which biodegradable materials can be obtained by rolling or calendering. The substance comprises a homogeneous mixture of a thermoplastic polyurethane resin, a carbohydrate, a second thermoplastic resin to make the substance calenderable which comprises polyvinyl chloride (PVC), and an additional biodegradable resin which is a biodegradable aliphatic polyester, preferably of the same nature as the polyurethane resin. For example, the substance could contain a polycaprolactone-based polyurethane, starch, PVC, and polycaprolactone.

International Patent application WO 91/13207, discloses biodegradable sheet structures based on paper substrates coated with a latex and subsequently dried. The latex comprises a colloidal suspension in water of essentially non-crystalline particles of a biodegradable polymer such as polyhydroxybutyrate or polyhydroxybutyrate/valerate copolymer.

European Patent Application EP-449041, discloses non-thermoplastic blends of cellulose hydrate with urea-based polyurethanes prepared by mixing viscose with the polyurethane, gelling the mixture at above 40° C. with an acidic coagulant and regenerating agent, treating the gel with plasticizers, and finally drying the film. The films are said to be useful as packaging films, refuse sacks, mulch films, diaper covers, and the like.

U.S. Pat. No. 5,037,410, discloses diaper backsheets composed of 20–80% by weight unvulcanized C4-C6 diene elastomer, for example natural rubber, 5–20% modifier such as starch, 1–40% inorganic fillers, 0–40% styrene-based resin, plus waxes, and other ingredients. The backsheets are reported to have tensile strengths above 200 grams per inch of width.

European Patent Application 91106627.2, discloses a biodegradable latex web material suitable for diaper backsheets and mulch films. The materials are prepared by impregnating a cellulose fiber or paper web with a carboxylated latex comprising both synthetic polymers such as styrene-butadiene rubber and PVC, and natural polymers such as starch, proteins and natural rubber. Tensile strengths ranging from 189 to 304 kg./sq. cm. are cited.

U.S. Pat. No. 3,952,347, discloses a biodegradable barrier film comprising a non-biodegradable and water-insoluble film-forming material having a biodegradable material homogeneously dispersed throughout its structure. Water-insoluble polyvinyl alcohol and polyethylene are used for the film forming materials, while starch, dextrin, and collagen are used for the biodegradable components.

U.S. Pat. No. 4,964,857, discloses biodegradable diapers based on multiple layers of moisture resistant paper interspersed with layers of absorbent materials. The moisture resistant paper is specified as one coated with a naturally occurring wax such as beeswax.

SUMMARY OF THE INVENTION

The present invention encompasses flexible biodegradable films comprising multilayer combinations of biodegradable polymers. The biodegradable polymers are selected from the categories of moisture sensitive polymers, thermally sensitive polymers, mechanically limited polymers, polymers difficult to process into films, hydrolytically cleavable aromatic/aliphatic polyester copolymers, oxidized ethylene/carbon monoxide copolymers, high melting aliphatic polyesters, and degradable elastomers. The films of the present invention comprise two or more components selected from the above-mentioned categories. Optionally, the multilayer films may further comprise additional adhesive tie layers. The biodegradable polymers are combined in various ways to overcome the deficiencies of the individual components, yet at the same time to impart specific performance properties to the film. The films are suitable for use in disposable absorbent products including diapers, adult incontinent pads, sanitary napkins, and pantiliners.

As will be discussed in detail hereinafter, the biodegradable, liquid impervious multilayer films of the present invention have:

a) a machine direction (MD) tensile modulus from about 10,000 to about 100,000 lbs./sq. in. (6.895×10$^8$ dynes/sq. cm. to 6.895×10$^9$ dynes/sq. cm.);

b) a MD tear strength of at least 70 grams per 25.4 microns of thickness;

c) a cross machine direction (CD) tear strength of at least 70 grams per 25.4 microns of thickness;

d) an impact strength of at least 12 cm. as measured by falling ball drop;

e) a moisture transport rate less than about 0.0012 grams per square centimeter per 16 hours;

f) a modulus at 60° C. of at least 5.52×10$^7$ dynes/sq. cm. (800 lbs./sq. in. ); and g) a thickness from about 12 microns to about 75 microns.

The present invention also encompasses disposable absorbent articles comprising a liquid pervious topsheet, a liquid impervious backsheet, and an absorbent core encased between the topsheet and the backsheet, said articles being characterized in that said backsheet comprises a flexible biodegradable film derived from multilayer combinations of biodegradable polymers and blends of biodegradable polymers as will be described hereinafter.

DETAILED DESCRIPTION OF THE INVENTION

The films used to prepare the backsheet materials and other biodegradable products employed herein are derived from combinations of two or more biodegradable polymers. In general, the biodegradable polymers alone do not meet all the performance standards required of backsheet materials. The films of the current invention may comprise multilayer combinations of various biodegradable polymers, selected and compounded such that the deficiencies of the individual components are overcome.

The individual polymers are thermoplastic and may be combined into multilayer structures by coextrusion, extrusion coating, lamination, or other techniques. The individual polymers in each layer may be present in their pure state or blended with other biodegradable components such that the entire structure meets the performance standards required of backsheet materials.

The individual polymers selected for the films of the current invention are biodegradable polymers obtained from many sources, both natural and synthetic. Each polymer has certain attributes which render it biodegradable. However, many of these attributes prevent the polymer from being used singularly as a backsheet material.

For example, some biodegradable polymers are very water sensitive and lose significant strength or even dissolve when exposed to aqueous media. Examples include interpenetrated networks of destructurized starch, polyvinyl alcohol and related derivatives, various hydroxy propyl cellulose derivatives, and polyethylene oxide.

Other biodegradable polymers are thermally sensitive due to their low melting points or glass transition temperatures, generally 65° C. or lower. The Vicat softening temperatures of such materials can occur at temperatures much lower than 65° C., often below 45° C. Examples include many aliphatic polyesters such as polycaprolactone, polyethylene adipate, polybutylene glutarate, and polypropylene succinate.

Still other polymers have mechanical deficiencies and may be too stiff, too soft, or suffer from poor tensile and/or tear strengths. The elongational properties of some polymers are also insufficient to meet backsheet performance standards. Examples include cellulosic materials such as cellophane, cellulose esters, and blends of cellulose esters with aliphatic polyesters.

Other polymers are difficult to process by conventional means into films suitable for backsheet applications. In some cases, the crystallization rates of the polymers are too slow or the flow properties of the polymers make film processing difficult. Examples include polyhydroxyalkanoates like polyhydroxybutyrate or polyhydroxybutyrate/valerate copolymers.

Some biodegradable polymers meet many or all the physical property requirements of backsheet applications alone but do not degrade fast enough to break up into small fragments in the early stages of composting. Hence, there is a strong likelihood such polymers would be screened out of the compost stream and not become part of the final compost. Examples of such components include hydrolytically cleavable polyesters such as certain aromatic/aliphatic polyester copolymers, oxidized ethylene/carbon monoxide copolymers, and high melting aliphatic polyesters with melting points above 65° C.

The biodegradable polymers used to fabricate the films of the current invention may also be combined with optional ingredients such as biodegradable elastomers, tie layers, pigments, processing aids and the like. Each of these polymers is described in detail below.

I. MOISTURE SENSITIVE POLYMERS

A. DESTRUCTURIZED STARCH COMPOSITIONS

Thermoplastic, biodegradable compositions based on interpenetrated networks of starch with a synthetic component such as an ethylene/vinyl alcohol (EVOH) copolymer are described in International Patent Applications WO 90/10671, WO 90/110069.3, WO 91/02025, WO 91/02024, WO 91/02023, European Patent Application 90810533.1, and U.S. Pat. No. 5,095,054, all herein incorporated by reference. Such materials are available commercially from Novamont under the tradename Mater-Bi and from Warner Lambert under the tradename Novon. These materials comprise greater than 50% starch by weight and are, thus, very sensitive to moisture vapor levels in the ambient atmosphere as well as direct contact with liquid water.

Films comprising only the interpenetrated network of starch and a synthetic component can be extruded with very good mechanical properties initially. However, these properties vary considerably with humidity. For example, the modulus of a Mater-Bi film (Type AFO5H) decreases by about 50% as the relative humidity changes from about 20% to 90%. Although such sensitivity to humidity is a reversible process, it makes the film inconsistent on a day-to-day basis to the degree that converting operations and end-user performance are negatively affected.

Mater-Bi films also absorb water to a high degree, typically about 30% of their initial weight. In addition to lowering the strength of the film significantly, the high water absorption also leads to very high moisture transmission through the film, for example about 0.0024 grams/sq. cm./16 hours through a 30 micron film. This is beneficial in some applications where breathability is desired. However, high moisture transmission may not be desirable if the film is expected to contain large quantities of fluids, as in the case of a diaper backsheet. High water permeation can lead to excessive condensation on the outside of the backsheet leaving it cold and wet feeling to the touch.

Novon films can also be extruded with good initial properties. Some, however, like Novon grade M0014 are so sensitive to water they quickly fall apart, disperse into smaller particles, and virtually dissolve when contacted or immersed in liquid water.

Destructurized starch compositions find use in the present invention as internal core layers in multilayer films obtained by coextrusion or lamination with moisture resistant polymers selected from the group consisting of thermally sensitive polymers, mechanically limited polymers:, hydrolytically cleavable aromatic/aliphatic polyester copolymers, oxidized ethylene/carbon monoxide copolymers, and high melting aliphatic polyesters, elastomers, and mixtures thereof.

B. POLYVINYLALCOHOL (PVA) AND DERIVATIVES

Chemically, PVA can be described as a polyhydric alcohol with hydroxyl groups extending from alternate carbon atoms. It is represented structurally as follows:

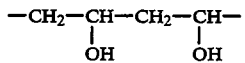

PVA is prepared via hydrolysis of polyvinylacetate. Depending on the degree of hydrolysis, PVA can be obtained in grades which are soluble in both cold and hot water or hot water only.

Unmodified PVA is not thermoplastic. However, when PVA is plasticized with appropriate additives, thermoplastic materials can be obtained. External plasticizers such as glycerol, ethylene glycol, and some of the lower polyethylene glycols are effective plasticizers for PVA.

The biodegradability of PVA is well documented. A brief overview on its biodegradation can be found in "Handbook of Water-Soluble Gums and Resins", R. L. Davidson, Editor. Chapter 20, p 20-17, herein incorporated by reference.

Thermoplastic PVA compositions suitable as components for the films of the present invention are sold by Air Products and Chemicals, Inc. of Allentown, Pa., under the tradename Vinex. Vinex resins are internally plasticized compositions achieved by copolymerizing PVA with a poly(alkyleneoxy) acrylate. More detailed disclosures of these materials are given in U.S. Pat. Nos. 4,618,648, and 4,675,360, both herein incorporated by reference. Still another method for making thermoplastic polyvinylalcohol compositions via the incorporation of polyurethanes is disclosed in U.S. Pat. No. 5,028,648, herein incorporated by reference. The biodegradation of Vinex compositions is disclosed in an Air Products Technical Bulletin entitled "Measurement of the Biodegradability of Vinex Resins by Controlled Respirometry" by J. Kramer, herein incorporated by reference.

A Vinex 1000 series, 2000 series, and 3000 series exist. The 1000 series are fully hydrolyzed grades which are insoluble in cold water, but soluble in hot water. The 2000 and 3000 series are soluble in both hot and cold water. All three series of Vinex resins can be employed in films of the present invention. Especially preferred are the 2000 series. Such materials, for example Vinex 2034, form tough tear resistant films which, if not for their water solubility, would meet the mechanical strength requirements for biodegradable backsheets of absorbent articles.

In the multilayer films of the current invention, the Vinex materials can be used in individual layers as blends with one or more moisture resistant biodegradable polymers selected from the group consisting of thermally sensitive polymers, mechanically limited polymers, polymers difficult to process into films, hydrolytically cleavable aromatic/aliphatic polyester copolymers, oxidized ethylene/carbon monoxide copolymers, and high melting aliphatic polyesters, and elastomers. They are also used as internal core layers in coextruded or laminated multilayer films having outer layers made from moisture resistant polymers selected from the group consisting of thermally sensitive polymers, mechanically limited polymers, hydrolytically cleavable aromatic/aliphatic polyester copolymers, oxidized ethylene/carbon monoxide copolymers, and high melting aliphatic polyesters, elastomers, and mixtures thereof.

C. HYDROXYPROPYL CELLULOSE (HPC)

HPC is a non-ionic cellulose ether with an unusual combination of properties among cellulose derivatives. These include solubility in both water and polar organic solvents as well as plastic flow properties that permit its use for molded and extruded articles such as films. As described in aforementioned "Handbook of Water Soluble Gums and Resins" (Chapter 13), herein incorporated by reference, the plastic flow properties of HPC enable it to be used as a base material in extrusion, blow, or injection molding, and film-making operations. Thermally processed products formed by these methods retain their water solubilities, are biodegradable, and can even be made to be edible.

The chemical cellulose used to prepare HPC is derived from wood pulp or cotton linters. The cellulose is treated with aqueous sodium hydroxide to form alkali cellulose which, in turn, is reacted with propylene oxide to yield the following empirical structure:

where n has a range of 3 to 4.5 and x has a range of 150 to 3000. Commercially, HPC is available from Hercules Inc. under the tradename KLUCEL.

Due to their water solubility, high stiffness, and low tear strength, HPC films alone are not acceptable for use as backsheet films for absorbent articles. HPC can be employed in blends in individual layers of multilayer films at low levels, typically 33 weight percent or less, with moisture resistant polymers, where it imparts temperature resistance and resistance to blocking. Small amounts of plasticizers, internal lubricants, and antioxidants can be used to improve the melt flow, mold release, and thermal stability of the polymer during processing. Suitable plasticizers include propylene glycol, glycerin, low molecular weight polyethylene glycols, and glycerol monostearate.

II. THERMALLY SENSITIVE POLYMERS

Since commercial composting operations typically achieve temperatures of about 60° C., biodegradable polymers with low thermal softening points or melting points may be included in the films of the current invention to help break the films down into smaller fragments early in the process. Moreover, such polymers may also biodegrade faster than higher melting components since they are essentially liquids at composting temperatures rather than solids. The rapid initial biodegradation and loss of these polymers from the film would also be expected to expose more of the higher melting polymers to hydrolytic agents and microorganisms thereby increasing their rate of biodegradation as well.

Aliphatic polyesters belong to the family of linear saturated polyesters. Many aliphatic polyesters are known to be biodegradable. Many also have melting points of about 65° C. or less. Although some types of low melting aliphatic polyesters can be processed directly into thin water resistant films, their melting points are too low to allow their use alone in many applications, for example, as backsheets for disposable absorbent articles.

Polycaprolactone is an example of a preferred biodegradable aliphatic polyester for use in the present invention. It is produced via the ring-opening polymerization of epsilon-caprolactone, a seven-membered ring compound. As described in Union Carbide Brochure F-60456 entitled "Tone Polymers", herein incorporated by reference, the polymerization is initiated with a diol (HO—R—OH, where R is an aliphatic segment) to produce polymers with the following structure:

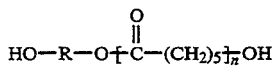

where n is the degree of polymerization.

Polycaprolactone polymers are available from Union Carbide Corporation under the tradename TONE in a variety of molecular weight grades. For example, TONE polymers P-300 and P-700 have degrees of polymerization of about 95 and 400 respectively, corresponding to molecular weights of about 10,000 and 40,000 grams per mole. TONE P-767 is prepared from a special high purity grade of caprolactone monomer and has an average molecular weight of about 43,000 grams per mole. TONE P-787 has an even higher average molecular weight of about 80,000 grams per mole.

Polycaprolactone polymers having molecular weights of about 40,000 and greater can be melt processed into strong water resistant films. Except for their low melting point of about 60° C. (140° F.), these films could function as backsheets for absorbent articles. Because of their low melting points, backsheets consisting of 100% polycaprolactone would have difficulty, for example, withstanding the high temperatures encountered when hot glue is applied to the diaper during the manufacturing process. In addition, during shipping and/or warehouse storage, temperatures of 60° C. can be reached. Backsheets consisting of 100% polycaprolactone would be difficult to stabilize in such an environment and might distort, stick to one another, or even melt.

In the multilayer films of the present invention, polycaprolactone can be used as a blend component in individual layers, or as outer skin layers surrounding a moisture sensitive core layer, or as a inner core layer itself, surrounded by outer layers selected from the category of thermally resistant polymers such as mechanically limited polymers, hydrolytically cleavable aromatic/aliphatic polyester copolymers, oxidized ethylene/carbon monoxide copolymers, high-melting aliphatic polyesters, and mixtures thereof.

In the films of the present invention, polycaprolactone polymers having an average molecular weight of 40,000 or more are preferred. Especially preferred are polycaprolactone polymers having an average molecular weight of about 80,000 grams per mole (e.g., TONE P-787).

Other types of low melting aliphatic polyesters suitable for use in the present invention are derived from the reaction of an aliphatic dicarboxylic acid and a diol. As described in "An Overview of Plastics Degradability," by Klemchuk, published in Modern Plastics, (August, 1989) and incorporated herein by reference, many of these polyesters are biodegradable since they are susceptible to enzymatic hydrolysis. Moreover, the acid and alcohol fragments of the hydrolysis are also easily assimilated by microorganisms.

Such polyesters are prepared via the generalized reaction shown below:

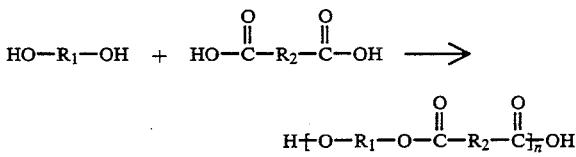

where $R_1$ is a linear methylene chain —$(CH_2—)_x$ with $2<x<10$, $R_2$ is also a linear methylene chain —$(CH_2—)_y$ with $2<y<10$; and n is the degree of polymerization. Examples of these types of aliphatic polyesters include:

Polyethylene adipate where $x=2$ and $y=4$; $Tm=50°$ C.
Poly (1,3 propanediol adipate) where $x=3$ and $y=4$; $Tm=38°$ C.
Poly (1,4 butanediol adipate) where $x=4$ and $y=4$; $Tm=48°$ C.
Poly (1,4 butanediol sebacate) where $x=4$ and y:8; $Tm=64°$ C.
Poly (1,3 propanediol succinate) where $x=3$ and $y=2$; $Tm=47°$ C.
Poly (1,4 butanediol glutarate) where $x=4$ and $y=3$; $Tm=47°$ C.

Further examples of thermally sensitive aliphatic polyesters with melting points less than 65° C. can be found in "Polymer Handbook, Third Edition" by J. Brandrup and E. H. Immergut published by John Wiley & Sons, in Section VI, pages 56 through 67, herein incorporated by reference.

III. POLYMERS DIFFICULT TO PROCESS INTO FILMS

Another family of biodegradable aliphatic polyesters includes those derived from alpha-hydroxy carboxylic acids. This family of poly (alpha-hydroxy alkanoates) includes synthetic polymers such as polylactates from lactic acid and naturally derived polymers such as polyhydroxybutyrate (PHB) polymers and polyhydroxybutyrate/valerate (PHBV) copolymers. Preferred examples of polyhydroxybutyrate homopolymer and polyhydroxy butyrate/valerate copolymers are described in U.S. Pat. No. 4,393,167, Holmes et al., issued Jul. 12, 1983, and U.S. Pat. No. 4,880,592, Martini et al., issued Nov. 14, 1989, both references incorporated herein by reference. PHBV copolymers have the generalized structure shown below.

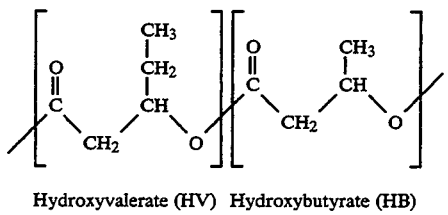

Hydroxyvalerate (HV)   Hydroxybutyrate (HB)

Such copolymers are commercially available from Imperial Chemical Industries under the tradename Biopol. The Biopol polymers are produced from the fermentation of sugar by the bacterium Alcaligenes eutrophus. PHBV polymers are currently produced with valerate contents ranging from about 5 to about 24 mole percent. Increasing valerate content decreases the melting point, crystallinity, and stiffness of the polymer. An overview of Biopol technology is provided in Business 2000+, (Winter, 1990), incorporated herein by reference.

Unfortunately PHBV copolymers are difficult to process directly into films because of their slow crystallization rate. This causes the film to stick to itself even after cooling to room temperature because a substantial fraction of the PHBV remains amorphous and tacky for long periods of time. In cast film operations, where the film is immediately cooled on chill rolls after leaving the film die, molten PHBV often sticks to the rolls restricting the speed at which the film can be processed, or even preventing the film from being collected. In blown films, residual tack of the PHBV causes the tubular film to stick to itself after it has been cooled and collapsed for winding.

International Patent Application 86309586.5, describes a means of achieving a PHBV monolayer film for diaper backsheet applications by coextruding the PHBV between two layers of sacrificial polymer, for example a polyolefin, stretching and orienting the multilayer film, and then stripping away the polyolefin layers after the PHBV has had time to crystallize. The remaining PHBV film is then laminated to either water soluble films (PVA preferred) or water insoluble films such as polyvinylidene chloride or other polyolefins.

In the multilayer films of the present invention, such drastic processing methods are avoided. The PHBV can be employed as a blend component in one or more of the layers with one or more polymers selected from the categories of moisture sensitive polymers, thermally sensitive polymers, mechanically limited polymers, hydrolytically cleavable aromatic/aliphatic polyester copolymers, oxidized ethylene/carbon monoxide copolymers, high melting aliphatic polyesters, and elastomers. If used in an outer layer of a multilayer film, the PHBV component is generally employed in an amount less than about 40% by weight. This allows the other components to function as the continuous phase in the blend and overcome the tackiness and processing difficulties of the PHBV as described above.

The PHBV may also be coextruded as an internal layer surrounded by outer layers selected from the categories of thermally sensitive polymers, mechanically limited polymers, hydrolytically cleavable aromatic-/aliphatic polyester copolymers, oxidized ethylene/carbon monoxide copolymers, and high melting aliphatic polyesters, and mixtures thereof. In the films of the current invention, the external layers are not stripped away from the PHBV layer. They remain as an integral part of the biodegradable film.

IV. MECHANICALLY LIMITED POLYMERS

A. CELLULOSE ESTERS

Cellulose esters are produced by the chemical modification of cellulose and include the family of cellulose acetates (CA), cellulose acetate propionates (CAP), and cellulose acetate butyrates (CAB). As described in the 1990 Modern Plastics Encyclopedia (McGraw-Hill, pp. 23-24), herein incorporated by reference, cellulose esters are prepared by reacting cellulose with particular acids and acid anhydrides, generally in the presence of a sulfuric acid catalyst. In the case of CA, the reaction is first carried out with acetic acid and acetic anhydride to produce cellulose triacetate, which contains nearly 100% acetyl substitution or, in other words, a degree of substitution of about 3.0. The triacetate is then partially hydrolyzed to remove some of the acetyl groups such that the CA product contains about 38 to 50% acetyl substitution.

CAP and CAB are made by substituting propionic acid and propionic anhydride or butyric acid or butyric anhydride for some of the acetic acid and acetic anhydride. Plastic grades of CAP generally contain 39 to 47% propionyl and 2 to 9% acetyl content. Plastic CAB grades generally contain 26 to 39% butyryl and 12 to 15% acetyl content. Commercially, CA, CAB, and CAP are obtained from Eastman Chemical Products, Inc. under the tradename Tenite.

Although raw cellulose and its regenerated film (cellophane) and fiber (rayon) forms are readily biodegradable, the esterification of cellulose can make it quite stable to microbial attack. As described in "Polymer Degradation" by W. Schnabel (Macmillan, New York, 1981), herein incorporated by reference, this enhanced resistance to biodegradation results from the inability of cellulose-specific enzymes to attack the substituted portions of the polysaccharide. However, as described by Buchanan and Gardner in an Abstract of their paper entitled "The Fate of Cellulose Esters in the Environment: Aerobic Biodegradation of Cellulose Acetate" presented at the CELLULOSE '91 CONFERENCE held in New Orleans, La., Dec. 2-6, 1991, the rate of degradation of cellulose esters also depends upon the degree of substitution. For example, a CA with a 1.7 degree of substitution was found to biodegrade much faster than a CA with a 2.5 degree of substitution.

Fully formulated grades of cellulose esters may also contain plasticizers, heat stabilizers, and ultraviolet inhibitors. High levels of these stabilizers and inhibitors may further slow the rate of biodegradation of cellulose esters. Zero or very low levels of such stabilizers are generally preferred in biodegradable films.

Plasticized cellulose esters like CA, CAP, and CAB are thermoplastic and can be melt processed into thin films. Unless substantial levels of plasticizer are employed, the stiffness of such films is too high for them to be useful as backsheets for absorbent articles. Even in the presence of plasticizers, the tear propagation resistance of cellulose ester films is very low, typically below 20 grams per 25.4 microns of thickness in the machine direction.

In the multilayer films of the current invention, cellulose esters can be used in both inner or outer layers in blends with one or more biodegradable polymers selected from the category of moisture sensitive polymers, thermally sensitive polymers, hydrolytically cleavable aromatic/aliphatic polyester copolymers, oxidized ethylene/carbon monoxide copolymers, and elastomers.

Alternatively, in the multilayer films, cellulose esters can be coextruded as outer layers surrounding internal core layers selected form the categories of moisture sensitive polymers, thermally sensitive polymers, and elastomers. Tear strength can also be enhanced by laminating or extrusion coating thin cellulose ester films on to biodegradable non-woven fabrics such as rayon.

B. CELLULOSE ESTER BLENDS WITH OTHER BIODEGRADABLE POLYMERS

It is well known that cellulose esters form miscible blends with many aliphatic polyesters. U.S. Pat. No. 3,642,507, herein incorporated by reference, discloses the formulation of printing inks with improved flexibility by blending a cellulose ester with polycaprolactone. U.S. Pat. No. 3,922,239, herein incorporated by reference, also discloses the preparation of thermoplastic blends of cellulose esters and polycaprolactone and other cyclic ester polymers. The addition of the polyesters was found to lower the modulus of the blend significantly below that of the cellulose ester and to impart improved melt processability, toughness, and impact resistance.

More recently, blends of CAP and CAB with polyhydroxybutyrate (PHB) have been described by Ceccorulli, Pizzoli, and Scandola in an Abstract of a paper entitled "Blends of Cellulose Esters with Bacterial Poly(3-hydroxybutyrate)" presented at the aforementioned CELLULOSE '91 CONFERENCE, and herein incorporated by reference. Experimental evidence of miscibility was found up to 50% PHB. Crystallization of the PHB was found to be strongly inhibited by the presence of cellulose esters confirming intimate mixing of the blend components. Similar results are obtained if PHBV copolymers are employed in place of PHB.

Blends as described above are thermoplastic and can be processed into thin flexible films with stiffness levels appropriate for backsheet films. However, the tear propagation resistance of such films alone is still deficient compared to those normally used to construct absorbent articles such as disposable diapers. As will be discussed later, the inclusion of certain biodegradable elastomers can improve the tear strength of said blends significantly. In multilayer structures, cellulose ester blend layers can be coextruded as moisture resistant outer layers surrounding moisture sensitive inner core layers or coextruded as thermally resistant outer layers surrounding thermally sensitive internal core layers. Alternatively, they can be laminated or extrusion coated onto biodegradable non-woven fabrics such as rayon to make structures with better tear strength.

V. HYDROLYTICALLY CLEAVABLE POLYESTERS

A. AROMATIC/ALIPHATIC POLYESTER COPOLYMERS

Aromatic polyesters such as polyethylene terephthalate (PET) and polybutylene terephthalate (PBT) are leading examples of high performance polyesters for film, fiber, or injection molding applications. Although the monomeric starting materials for such polyesters are known to be biodegradable, neither PET or PBT are considered to be biodegradable polymers. As homopolymers, both polyesters tend to crystallize to relatively high extents making them extremely difficult to hydrolyze except under conditions of very high temperature in the presence of water, for example in the melt state, or in the presence of strongly acidic or basic media. Such conditions do not exist in municipal composting operations. In the case of PET, not only is a significant fraction of the polymer in a crystalline state, but the softening point or glass transition temperature (about 80° C.) of the remaining noncrystalline or amorphous fraction is also above typical composting temperatures. Hence, even the amorphous fraction will be resistant to hydrolysis in a composting operation.

Several means of making aromatic polyesters more readily hydrolytically cleavable, and hence more likely to be biodegradable, have recently been described. U.S. Pat. No. 5,053,482, issued to Tietz on Oct. 1, 1991, describes polyesters based on polyethylene terephthalate (PET) copolymerized with diethylene glycol and 5-sulfoisophthalic acid wherein the glass transition temperature of the copolymers is preferrably reduced to below 65° C., within the range of normal composting operations. The copolymers are said to be suitable for producing films and fibers for use in disposable articles such as diapers. Although hydrolysis of the copolymer films and fibers is shown to take place in boiling water (100° C.), evidence of the extent or rate to which true biodegradation occurs is not presented.

Yet another approach to increasing the hydrodegradability of aromatic polyesters is described in International Patent Application WO 91/02015, published Feb. 21, 1991, herein incorporated by reference. In this case, hydrodegradable polyesters based on the random copolymerization of aromatic and aliphatic polyesters is disclosed. More specifically, the random copolymers are comprised of aromatic polyesters such as PET or PBT randomly interrupted with aliphatic hydrodegradable link polymers such as polyglycolic acid, polylactic acid, polycaprolactone, polyhydroxybutyrate, polyhydroxybutyrate/valerate, polybutylene oxalate, polyethylene adipate, polyethylene carbonate, polybutylene carbonate, and other polyesters containing silyl ethers, acetals, or ketals. Preparation of the copolymers is carried out by either ester interchange reactions of the appropriate monomeric species or by transesterification reactions between two homopolymers in the presence of an appropriate catalyst.

In addition to the aforementioned aliphatic link polymers, other aliphatic polyesters may also be appropriate for producing aromatic/aliphatic polyester copolymers. These include aliphatic polyesters selected from the group of oxalates, malonates, succinates, glutarates, adipates, pimelates, suberates, azelates, sebacates, nonanedioates, glycolates, and mixtures thereof.

In both the above cases, it is assumed true biodegradation will occur once the copolymers hydrolyze to very low molecular weight oligomers or monomeric species. However, the rate to which this occurs in a composting environment at temperatures below 65° C. and at relatively small deviations from neutral pH may be too slow to ensure the breakup of films before they are removed by screening, air classification, or other separations method. To enhance the initial breakup and ultimate degradation of such polyester copolymers, blending with one or more rapidly biodegradable polymers can be employed, said more rapidly biodegradable polymers selected from the categories of moisture sensitive polymers, thermally sensitive polymers, polymers difficult to process into films, and mixtures thereof. In such blends, the aromatic/aliphatic polyester copolymer comprises from about 60 weight percent to about 95 weight percent of the blend. Such blends may be used in one or more layers of the multilayer films of the present invention. Alternatively, the aromatic/aliphatic polyester copolymers themselves can be coextruded as outer layers surrounding moisture sensitive polymers, themally sensitive polymers, polymers difficult to process into films, or elastomers.

B. OXIDIZED ETHYLENE-CARBON MONOXIDE COPOLYMERS

Photodegradable polymers based on random copolymers of ethylene and carbon monoxide are used commercially in beverage can rings and other items which may often be discarded in the environment as litter. Such copolymers are disclosed in U.S. Pat. No. 2,495,286, issued to Brubaker, herein incorporated by reference. In order to provide acceptable rates of photodegradation, only a small proportion (generally 1 to 3 mole percent) of carbon monoxide or other carbonyl functionality needs to be incorporated into the polymer. Decomposition of such plastics begins as soon as the plastic is exposed to sunlight although there may be a delay period before significant breakdown of important physical properties are noted. As the polymer chains decrease in molecular weight, the plastic material macroscopically breaks down into smaller fragments which become more and more susceptible to microbial attack and hence biodegradation.

In the absence of sunlight, for example, in a commercial composting operation, this photodegradative process will not be initiated and the plastic articles containing photodegradable linkages will not break down in both molecular weight and size rapidly to become part of the final compost. Rather, they will likely be screened out or otherwise separated from the compost stream along with other non-biodegradable materials.

Recently, it has been found that ethylene/carbon monoxide polymers can be oxidized to yield a new type of aliphatic polyester. U.S. Pat. No. 4,929,711, herein incorporated by reference, describes a process for converting a polyketone, for example a ethylene/carbon monoxide (ECO) copolymer, to a polyester. The process involves the reaction of the ECO copolymer with an organic peroxyacid oxidizing agent in an inert liquid medium at temperatures between −20° C. to 150° C. Substantially all or only a portion of the ketone functionality can be converted to ester groups depending upon the reaction conditions.

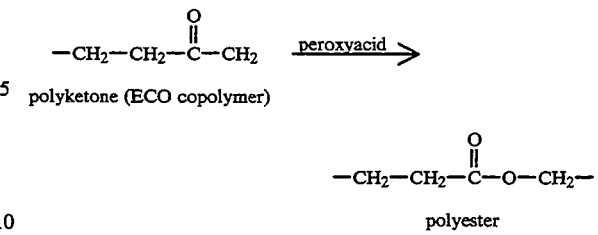

Subsequent U.S. Pat. No. 4,957,997, expands this process to polyketones containing pendant functional groups obtained by the copolymerization of carbon monoxide with vinyl or vinyl idene monomers. The vinyl or vinyl idene monomer may have at least one functional group containing one or more oxygen, nitrogen, sulfur, or halogen atoms.

The new polyesters described in these patents may originate from polyketones containing 0.5 to 20 weight percent carbon monoxide and having a molecular weight from about 10,000 to about 1,000,000 grams per mole. After oxidation to the corresponding polyesters, the materials are capable of being hydrolyzed to lower molecular weight fragments. The rate and extent to which both hydrolytic and microbial degradation occur depend on the number of ester groups present and the average molecular weight of the polymer between ester groups. The lower the molecular weight fragments resulting from hydrolysis become, the more susceptible they become to microbial attack and biodegradation. Preferably, the average molecular weight of the polymer chains between ester groups is below 1000 grams per mole. Most preferably, the average molecular weight between ester groups is below about 500 grams per mole.

Oxidized ECO copolymers have excellent moisture resistance and processability but their physical properties, particularly elongation to break in tension, at lower molecular weights, may not be sufficient for backsheets of absorbent articles. However, they are useful in multilayer films as moisture resistant outer layers surrounding moisture sensitive internal core layers, as thermally resistant outer layers on thermally sensitive internal core layers, as rapidly crystallizing outer layers on slowly crystallizing polymers which are difficult to process into films, and as non-blocking outer layers on elastomeric core layers. As mentioned in previous sections of this application, oxidized ECO copolymers are useful also as blend components in individual layers where they impart heat resistance and moisture resistance.

C. HIGH MELTING ALIPHATIC POLYESTERS

Yet another family of hydrolytically cleavable and biodegradable polyesters are high melting aliphatic polyesters defined, herein, as those having glass transition temperatures or melting points above 65° C. Such materials may not undergo initial decomposition and breakup during the early stages of composting since the crystalline fraction of these materials, or the amorphous fraction, or both the crystalline and amorphous fractions may be below their melting points or glass transitions at normal composting temperatures. High melting aliphatic polyesters can, however, be combined in blends or coextrusions with other more rapidly degrading materials, for example moisture sensitive or thermally sensitive polymers, to enhance their rates of initial decomposition and breakup. Examples of high melting aliphatic polyesters include polyethylene sebacate (Tm=76° C.), polyethylene succinate (Tm=108° C.), and polyhexamethylene sebacate (Tm=78° C.). Further examples can be found in the aforementioned "Polymer Handbook—Third Edition" Section VI, pages 56 through 67, previously incorporated herein by reference. The use of high melting aliphatic polyesters in blends and coextrusions with other biodegradable polymers has been discussed in previous sections of this application.

VI. ELASTOMERS

In the case of the mechanically deficient materials (cellulose esters and cellulose ester blends with various aliphatic polyesters) discussed earlier, it was noted their main deficiency was in tear strength. One way of improving the tear strength of films made from such materials is to incorporate a suitable thermoplastic elastomer (TPE) into the material by, for example, melt blending. A thermoplastic elastomer is a material that combines the processability of a thermoplastic with the functional performance and properties of a conventional thermosetting elastomer as discussed in Modern Plastics Encyclopedia, 1990, pp 122-131, herein incorporaated by reference. Commercially, there are 6 generic classes of TPE: styrenic block copolymers, polyolefin blends, elastomeric alloys, thermoplastic polyurethanes, thermoplastic copolyesters, and thermoplastic polyamides.

For use in films of the present invention, any thermoplastic elastomer incorporated into the film must be biodegradable. From the aforementioned list of TPE classes, only a select group of thermoplastic polyurethanes, specifically aliphatic polyester-based polyurethanes, are generally recognized as being biodegradable.

Biodegradable polyurethanes can be prepared from low molecular weight aliphatic polyesters derived from epsilon-caprolactone or the reaction products of a diol-dicarboxylic acid condensation. In general, these polyesters have molecular weights less than 10,000 grams per mole and frequently as low as 1000 to 2000 grams per mole. Examples of biodegradable polyester urethanes derived from polyethyleneglycol adipate, poly (1, 3-propanediol adipate) and poly (1, 4-butanediol adipate) are disclosed in "The Prospects for Biodegradable Plastics" by F. Rodriguez (Chem Tech, July—1971) incorporated herein by reference.

Aliphatic polyester urethanes are available from Morton International, Inc. under the tradename Morthane. When blended with other biodegradable polymers such as moisture sensitive polymers, thermally sensitive polymers, mechanically limited polymers, hydrolytically cleavable aromatic/aliphatic polyester copolymers, oxidized ethylene/carbon monoxide copolymers, high melting aliphatic polyesters, and mixtures thereof, they lower modulus, increase tear and impact strength, and impart moisture resistance. In multilayer structures, aliphatic polyester urethanes can be employed both as blend components in individual layers and alone as thin layers between other biodegradable polymers including moisture sensitive polymers, thermally sensitive polymers, mechanically limited polymers, hydrolytically cleavable aromatic/aliphatic polyester copolymers, oxidized ethylene/carbon monoxide copolymers, high melting aliphatic polyesters, and mixtures thereof, to impart increased tear and impact strength.

Procedures for synthesizing another type of TPE suitable for imparting improved toughness and tear strength to cellulose ester and cellulose ester blend films are disclosed in U.S. Pat. No. 3,585,257, issued to Mueller et al., and herein incorporated by reference. Block copolymers of polycaprolactone with polydienes such as polyisoprene and polybutadiene are disclosed in which the polycaprolactone content can be varied from about 20 to about 80 weight percent and the diene content varied from about 80 to about 20 weight percent. Copolymers having tensile strengths in the range between 245 and 2000 pounds per square inch and elongations to break in the range from 400 to 560 percent are obtained.

Block copolymers can be prepared having various architectures. For example an A-B diblock copolymer comprises a block of polymer A segments coupled to a block of B polymer segments. An A-B-A triblock copolymer comprises a block of B segments coupled to a block of A segments at each of its terminal ends. An $-(A-B)_n-$ multiblock copolymer comprises alternating sequences of A and B segments where n=2, 3, etc.

For toughening and increasing the tear strengths of films of the present invention, A—B—A triblock or $-(A-B)_n-$ multiblock copolymers in which polycaprolactone segments comprise the A blocks and n=2, 3, etc. are generally preferred. Simple diblock A—B copolymers do not impart significant tear strength improvement to films of the present invention. Especially preferred are triblock copolymers in which the polycaprolactone segments comprise from about 10 to about 60 weight percent of the copolymer and the polydiene segments comprise from about 90 to about 40 weight percent of the copolymer. To achieve the desired tear strength enhancement the copolymers are melt compounded with a cellulose ester or cellulose ester blend such that the copolymer comprises from about 30 to about 70 weight percent of the total composition.

VII. TIE LAYERS

Tie layer resins are interlaminar bonding agents used to adhere incompatible layers in coextruded or laminated film or sheet structures. In addition to bonding dissimilar polymer layers, tie layers are also used to bond polymers to metal foils, boardstocks, papers, or non-woven fabrics. Such materials are either coextruded between other polymers, or extrusion coated onto other substrates before being combined into composite structures through the application of heat and pressure. Coextrusion applications include cast film and sheet, blown film, and extrusion blow molded bottles. A wide variety of polyolefin-based tie layer resins are commercially available for use in non-biodegradable and hence non-compostable applications. Typical examples include the BYNEL CXA resins from DuPont and the PLEXAR family from Quantum Chemical. The tie resins offered by these suppliers cover a wide melt index range and are capable of bonding numerous base materials used in packaging applications as indicated in an article entitled "What Can Be Coextruded? The Sky's The Limit" appearing at pp 78-80 of the September, 1980 edition of Modern Plastics magazine, herein incorporated by reference.

The choice of tie resin for a particular application depends on various factors such as the chemical nature of the materials to be bonded, the melt viscosities of the other resins to be coextruded, stock processing temperatures, the type of process used, and the type of processing equipment. For compostable film applications, a tie resin, if used, must also be biodegradable. For the films of the present invention, it has been surprisingly found that polycaprolactone can be utilized as a biodegradable tie layer between certain biodegradable polymers. For example, a five layer biodegradable film, A-Tie-B-Tie-A, wherein the A layers are cellulose ester blends, the B layer is a water soluble polymer such as a thermoplastic polyvinylalcohol composition, and the tie layer is polycaprolactone can be achieved by coextruding all 5 layers simultaneously.

Alternatively, the polycaprolactone can be coextruded on either side of the thermoplastic polyvinyl alcohol layer to create a three layer film and laminated in a subsequent operation to the two cellulose ester blend layers through the simultaneous application of heat and pressure.

VIII. OPTIONAL COMPONENTS

In addition to the above-mentioned components, the backsheet films of the present invention may contain other components as may be, or later become, known in the art, including, but not limited to, antiblocking agents, antistatic agents, slip agents, pro-heat stabilizers, antioxidants, pro-oxidant additives, pigments, plasticizers, etc.

Antiblocking agents act to prevent film layers from sticking to one another when wound into a roll or when disposable articles are packaged in contact with one another. Typical antiblocking substances include concentrates of silica or talc blended with a polymeric material such as polyethylene or polycaprolactone. Reduction of blocking in the films of the present invention can also be obtained by loading the film surface with small particles or powders such as chalk, clay, silica, starch, and similar materials. Powdered polymeric materials (e.g., polytetrafluoroethylene) can also be used to reduce blocking when applied to the surface of films of the present invention. Such film surface treatments can be used to reduce blocking alone or in combination with other antiblock methods. The quantity of powder antiblock substance commonly added to the surface of a film, when used, is from about 0.5 g/m$^2$ to about 5 g/m$^2$.

Antistatic agents may be incorporated in films of the present invention; examples of such agents include ethoxylated amines and quarternary amine salts having organic constituents of about 12–18 carbon atoms in length. Agents of this type slowly diffuse to the surface of the film and, because of their ionic character, form an electrically conductive layer on the surface of the film. Antistatic agents commonly constitute from about 1% to about 5% of the weight of the films, when used.

Slip agents may be incorporated into the films of the present invention to reduce drag over rollers and other forming equipment. Examples of such agents are those commonly derived from amides of fatty acids having about 12 to 22 carbon atoms. Such agents may augment the antiblocking properties of the films of the present invention. Such slip agents are commonly incorporated in films from about 0.05% to about 3% of the weight of the films when used.

PERFORMANCE CRITERIA AND TEST METHODS

For a film to perform satisfactorily as a compostable disposable diaper backsheet, it must be made of resins or structures that are compostable and it must demonstrate the following properties of high strength, adequate fluid barrier, appropriate modulus or flexibility, and adequately high melting point.

The backsheets of disposable diapers must have sufficient strength both to process on a high speed disposable diaper converting machine and to provide a "wetproof" barrier in use on an infant. It must be sufficiently wetproof so that clothing or bedding, either that of the infant or of the caregiver, is not wet or soiled. It must have a modulus or flexibility that is, at the same time, low enough to be a soft, pleasing material to be used as the outer covering of an infant diaper yet high enough to handle easily on high speed disposable diaper converters without wrinkling, folding, or creasing. It must have sufficient resistance to heat such that it will not deform, melt, or permanently loose strength in typical hot storage conditions or loose its integrity on high speed disposable diaper converters which typically use hot melt adhesives to bond the components of a disposable diaper together.

It has been found that films that are sufficiently strong to be suitable as biodegradable backsheets for disposable diapers demonstrate two properties: (a) resistance to rupture from a dropped weight and (b) resistance to tearing in both the machine direction of manufacture and the cross-machine direction of manufacture. Acceptable biodegradable backsheets can withstand the drop of a spherical steel ball of about 19 millimeters in diameter and 27.6 to 28.6 gram mass from a height of 12 centimeters so that at least 50% of the tests result in no rupture of any size (deformation is acceptable). Preferred materials are those that exhibit 50% or less failures from a height of more than 20 centimeters. Similarly, acceptable biodegradable backsheets demonstrate an average tear propagation resistance of 70 gram per 25.4 micron thickness of material in both the machine direction and cross-machine direction of manufacture when a standard Elmendorf pendulum-type test device, such as Elmendorf Model No. 60-100, is employed against 16 plies of material which has been prepared with a cut or notch according to TAPPI Method T 414om-88. More preferable, are those backsheets that demonstrate tear propagation resistances of 200 or more grams per 25.4 micron thickness in the cross-machine direction because these are particularly good at avoiding a tendency to fail in use by splitting.

It has also been found that films of sufficient barrier to moisture transport are those that permit less than 0.0012 grams of synthetic urine to pass into an absorbent paper towel per square centimeter of area per 25.4 micron thickness for every 16 hours of time when the test film is located between the absorbent paper towel and a typical absorbent gelling material-containing diaper core and a pressure simulating that of a baby. The specific conditions of the test are that the area of the core is larger than that of the test material, the core is loaded with synthetic urine to its theoretical capacity and it is under a weight of about 35 g/sq. cm. (0.5 psi).

It has also been found that materials of sufficient heat resistance demonstrate a Vicat softening point of at least 45 degrees Centigrade. Vicat softening is tested using a Heat Distortion Apparatus Model No. CS-107 or equivalent and a modification of ASTM D-1525. The modification is in the preparation of the sample. A 19 millimeter by 19 millimeter size film of 4.5 to 6.5 micron thickness is prepared for Vicat needle penetration tests by melting the material to be tested into a mold of using a temperature of 120° C. and pressure of $7.031 \times 10^5$ g/sq.

cm. (10,000 psi) (using a Carver or similar press) for two minutes after a warmup period of at least 2 minutes. The Vicat softening point is the temperature at which a flat-ended needle of 1 sq. mm. circular cross section will penetrate the sample to a depth of 0.1 cm. under a load 1000 g using a uniform temperature rise rate of 50° C. per hour.

It has also been found that materials of sufficient machine direction modulus demonstrate a 1% secant-type modulus above at least about $6.895 \times 10^8$ dynes/sq. cm. (10,000 psi) and below about $6.895 \times 10^9$ dynes/sq. cm. (100,000 psi). The test is performed on an electronic tensile test machine such as the Instron Model 4201. A 2.54 cm. wide strip of material, preferably of 0.00254 cm. in thickness, is cut to a length of about 30 cm. with the longer dimension parallel to the machine direction of the material. The test strip is clamped into the jaws of the tensile testor so that the gauge or actual length of the material tested is 25.4 cm. The jaws are separated at a slow speed in the range of 2.54 cm. per minute to 25.4 cm. per minute and a stress-strain curve is plotted on a chart within an attached recording device. The 1% secant modulus is determined by reading the stress or tensile from the chart at the 1% elongation strain point. For example, the 1% strain point is achieved when the distance between jaws has increased by 0.254 cm. When the jaws are separating at the rate of 2.54 cm. per minute and the recording device is running at a speed of 25.4 cm. per minute, the 1% strain point will be located at a distance of 2.54 cm. from the initial point. The tensile response is divided by the thickness of the sample material if it is not 0.00254 cm. in thickness. Particularly soft, and therefore preferred, materials exhibit 1% secant moduli in the range of $6.895 \times 10^8$ to $2.068 \times 10^9$ dynes/sq. cm. (10,000 to 30,000 psi).

Since absorbent articles may experience temperatures as high as 140° F. (60° C.) during warehouse storage or shipping in trucks or railcars, it is important that the backsheet film and other components retain their integrity at these temperatures. Although it is expected that the modulus of the films will decrease somewhat between 20° C. and 60° C., the modulus should not decrease too far and allow the film to deform in the package before it reaches the end user.

For example, a polyethylene backsheet with a room temperature modulus of about $4 \times 10^9$ dynes/sq. cm. (58,000 psi) may have a 60° C. modulus of $1.2 \times 10^9$ dynes/sq. cm. (18,560 psi) which is acceptable. A softer polyethylene backsheet with a room temperature modulus of about $8.0 \times 10^8$ dynes/sq. cm.(11,600 psi) may have a 60° C. modulus of about $3.5 \times 10^8$ dynes/sq. cm. (5076 psi) which is still acceptable. In general, an acceptable backsheet film will have a 60° C. modulus of at least $5.52 \times 10^7$ dynes/sq. cm. (800 psi).

The modulus dependence on temperature, also called a modulus/temperature spectrum, is best measured on a dynamic mechanical analyzer (DMA) such as a Perkin Elmer 7 Series/Unix TMA 7 Thermomechanical Analyzer equipped with a 7 Series/Unix DMA 7 Temperature/Time software package, hereinafter referred to as the DMA 7, available from the Perkin-Elmer Corporation of Norwalk, Conn. Many other types of DMA devices exist, and the use of dynamic mechanical analysis to study the modulus/temperature spectra of polymers is well known to those skilled in the art of polymer characterization. This information is well summarized in two books, the first being "Dynamic Mechanical Analysis of Polymeric Material, Materials Science Monographs Volume 1" by T. Murayama (Elsevier Publishing Co., 1978) and the second being "Mechanical Properties of Polymers and Composites, Volume 1" by L. E. Nielsen (Marcel Dekker, 1974), both incorporated herein by reference.

The mechanism of operation and procedures for using the DMA 7 are found in Perkin-Elmer Users' Manuals 0993-8677 and 0993-8679, both dated May, 1991, and both herein incorporated by reference. To those skilled in the use of the DMA 7, the following run conditions should be sufficient to replicate the 60° C. modulus data presented hereinafter.

To measure the modulus/temperature spectrum of a film specimen, the DMA 7 is set to run in temperature scan mode and equipped with an extension measuring system (EMS). A film specimen approximately 3 mm. wide, 0.0254 ram. thick, and of sufficient length to allow 6 to 8 mm of length between the specimen grips is mounted in the EMS. The apparatus is then enclosed in an environmental chamber swept continuously with helium gas. Stress is applied to the film in the length direction to achieve a deformation or strain of 0.1 percent of the original length. A dynamic sinusoidal strain is applied to the specimen at a frequency of 5 cycles per second. In the temperature scan mode, the temperature is increased at a rate of 3.0° C./minute from 25° C. to the point where the specimen melts or breaks, while the frequency and stress are held constant. Temperature-dependent behavior is characterized by monitoring changes in strain and the phase difference in time between stress and strain. Storage modulus values in Pascals (1 Pascal=10 dynes/sq. cm.) are calculated by the computer along with other data and displayed as functions of temperature on a video display terminal. Normally the data are saved on computer disk and a hard copy of the modulus/temperature spectrum printed for further review. The 60° C. modulus is determined directly from the spectrum.

METHOD OF FILM MANUFACTURE

The multilayer films of the present invention used as biodegradable backsheets may be processed using conventional procedures for producing multilayer films on conventional coextruded film-making equipment. Where layers comprising blends are required, pellets of the above described components can be first dry blended and then melt mixed in the extruder feeding that layer. Alternatively, if insufficient mixing occurs in the extruder, the pellets can be first dry blended and then melt mixed in a precompounding extruder followed by repelletization prior to film extrusion.

In general, polymers can be melt processed into films using either cast or blown film extrusion methods both of which are described in "Plastics Extrusion Technology"—2nd Ed., by Allan A. Griff (Van Nostrand Reinhold—1976), herein incorporated by reference. Cast film is extruded through a linear slot die. Generally the flat web is cooled on a large moving polished metal roll. It quickly cools, and peels off this first roll, passes over one or more auxiliary cooling rolls, then through a set of rubber-coated pull or "haul-off" rolls, and finally to a winder. A method of making a cast backsheet film for the absorbent products of the current invention is described in Example 1 which follows.

In blown film extrusion the melt is extruded upward through a thin annular die opening. This process is also referred to as tubular film extrusion. Air is introduced through the center of the die to inflate the tube and causes it to expand. A moving bubble is thus formed which is held at constant size by control of internal air pressure. The tube of film is cooled by air blown through one or more chill rings surrounding the tube. The tube is next collapsed by drawing it into a flattening frame through a pair of pull rolls and into a winder. For backsheet applications the flattened tubular film is subsequently slit open, unfolded, and further slit into widths appropriate for use in absorbent products.

Both cast film and blown film processes can be used to produce either monolayer or multilayer film structures. For the production of monolayer films from a single thermoplastic material or blend of thermoplastic components only a single extruder and single manifold die are required.

For the production of multilayer films of the present invention, coextrusion processes are employed. Such processes require more than one extruder and either a coextrusion feedblock or multi-manifold die system or combination of the two to achieve the multilayer film structure.

U.S. Pat. Nos. 4,152,387, and 4,197,069, both herein incorporated by reference, disclose the feedblock principle of coextrusion. Multiple extruders are connected to the feedblock which employs moveable flow dividers to proportionally change the geometry of each individual flow channel in direct relation to the volume of polymer passing through said flow channels. The flow channels are designed such that at their point of confluence, the materials flow together at the same flow rate and pressure eliminating interfacial stress and flow instabilities. Once the materials are joined in the feedblock, they flow into a single manifold die as a composite structure. It is important in such processes that the melt viscosities and melt temperatures of the materials do not differ too greatly. Otherwise flow instabilities can result in the die leading to poor control of layer thickness distribution in the multilayer film.

An alternative to feedblock coextrusion is a multi-manifold or vane die as disclosed in aforementioned U.S. Pat. Nos. 4,152,387, 4,197,069, and in U.S. Pat. No. 4,533,308, herein incorporated by reference. Whereas in the feedblock system melt streams are brought together outside and prior to entering the die body, in a multi-manifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same linear flow rate, pressure, and desired width.

Since the melt flow properties and melt temperatures of biodegradable polymers vary widely, use of a vane die has several advantages. The die lends itself toward thermal isolation characteristics wherein polymers of greatly differing melt temperatures, for example up to 175° F. (80° C.), can be processed together. In this way a starch-based composition like Mater-Bi, with a maximum processing temperature of about 300° F. (149° C.), can be coextruded with a much higher temperature material like a cellulose ester with a processing temperature of 380° F. (193° C.).

Each manifold in a vane die can be designed and tailored to a specific polymer. Thus the flow of each polymer is influenced only by the design of its manifold, and not forces imposed by other polymers. This allows materials with greatly differing melt viscosities to be coextruded into multilayer films. In addition, the vane die also provides the ability to tailor the width of individual manifolds, such that an internal layer, for example a water soluble biodegradable polymer like Vinex 2034, can be completely surrounded by water insoluble materials leaving no exposed edges susceptible to water. The aforementioned patents also disclose the combined use of feedblock systems and vane dies to achieve more complex multilayer structures.

The multilayer films of the present invention may comprise two or more layers. In general, balanced or symmetrical three-layer and five-layer films are preferred. Balanced three-layer multilayer films comprise a center core layer and two identical outer layers, wherein said center core layer is positioned between said two outer layers. Balanced five-layer multilayer films comprise a center core layer, two identical tie layers, and two identical outer layers, wherein said center core layer is positioned between said two tie layers, and a tie layer is positioned between said center core layer and each outer layer. Balanced films, though not essential to the films of the present invention, are less prone to curling or warping than unbalanced multilayer films.

In three layer films, the center core layer may comprise 30 to 80 percent of the films' total thickness and each outer layer comprises 10 to 35 percent of the films' total thickness. Tie layers, when employed, each comprise from about 5 percent to about 10 percent of the films' total thickness.

ABSORBENT ARTICLES

Film materials used as liquid impervious backsheets in absorbent articles, such as disposable diapers, typically have a thickness of from 0.01 mm. to about 0.2 mm., preferably from 0.012 mm. to about 0.051 mm.

In general, the liquid impervious backsheet is combined with a liquid pervious topsheet and an absorbent core positioned between the topsheet and the backsheet. Optionally, elastic members and tape tab fasteners can be included. While the topsheet, the backsheet, the absorbent core and elastic members may be assembled in a variety of well known configurations, a preferred diaper configuration is described generally in U.S. Pat. No. 3,860,003, entitled "Contractible Side Portion for Disposable Diaper" which issued to Kenneth B. Buell on Jan. 14, 1975 and which patent is incorporated herein by reference.

The topsheet is compliant, soft-feeling, and non-irritating to the wearer's skin. Further, the topsheet is liquid pervious, permitting liquids to readily penetrate through its thickness. A suitable topsheet may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet is made of a hydrophobic material to isolate the wearer's skin from liquids in the absorbent core.

A particularly preferred topsheet comprises staple-length polypropylene fibers having a denier of about 1.5 such as Hercules type 151 polypropylene marketed by Hercules, Inc. of Wilmington, Del. As used herein, the term "staple-length fibers" refers to those fibers having a length of at least about 16 mm.

There are a number of manufacturing techniques which may be used to manufacture the topsheet. For example, the topsheet may be woven, non-woven, spun-bonded, carded, or the like. A preferred topsheet is carded and thermally bonded by means well known to those skilled in the fabrics art. Preferably, the topsheet has a weight from about 18 to about 25 $g/m^2$, a minimum dried tensile strength of at least about 400 g/cm. in the machine direction, and a wet tensile strength of at least about 55 g/cm. in the cross-machine direction.

The topsheet and the backsheet are joined together in any suitable manner. As used herein, the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. In a preferred embodiment, the topsheet and the backsheet are affixed directly to each other in the diaper periphery by attachment means such as an adhesive or any other attachment means as known in the art. For example, a uniform, continuous layer of adhesive, a patterned layer of adhesive, or an array of separate lines or spots of adhesive may be used to affix the topsheet to the backsheet.

Tape tab fasteners are typically applied to the back waistband region of the diaper to provide a fastening means for holding the diaper on the wearer. The tape tab fasteners can be any of those well known in the art, such as the fastening tape disclosed in U.S. Pat. No. 3,848,594, issued to Kenneth B. Buell on Nov. 19, 1974, the disclosure of which is incorporated herein by reference. These tape tab fasteners or other diaper fastening means are typically applied near the corners of the diaper.

Preferred diapers have elastic members disposed adjacent the periphery of the diaper, preferably along each longitudinal edge so that the elastic members tend to draw and hold the diaper against the legs of the wearer. The elastic members are secured to the diaper in an contractible condition so that in a normally unrestrained configuration the elastic members effectively contract or gather the diaper. The elastic members can be secured in an contractible condition in at least two ways. For example, the elastic members may be stretched and secured while the diaper is in an uncontracted condition. Alternatively, the diaper may be contracted, for example, by pleating, an elastic member secured and connected to the diaper while the elastic members are in their relaxed or unstretched condition.

The elastic members may take a multitude of configurations. For example, the width of the elastic members may be varied from about 0.25 mm. to about 25 mm. or more; the elastic members may comprise a single strand of elastic material or the elastic members may be rectangular or curvilinear. Still further, the elastic members may be affixed to the diaper in any of several ways which are known in the art. For example the elastic members may be ultrasonically bonded, heat and pressure sealed into the diaper using a variety of bonding patterns, or the elastic members may simply be glued to the diaper.

The absorbent core of the diaper is positioned between the topsheet and backsheet. The absorbent core may be manufactured in a wide variety of sizes and shapes (e.g., rectangular, hour-glass, asymmetrical, etc.) and from a wide variety of materials. The total absorbent capacity of the absorbent core should, however, be compatible with the designed liquid loading for the intended use of the absorbent article or diaper. Further, the size and absorbent capacity of the absorbent core may vary to accommodate wearers ranging from infants through adults.

A preferred embodiment of the diaper has a hourglass shaped absorbent core. The absorbent core is preferably an absorbent member comprising a web or batt of airfelt, wood pulp fibers, and a particulate absorbent polymeric composition disposed therein.

Other examples of absorbent articles according to the present invention are sanitary napkins designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is readily adapted are shown in U.S. Pat. No. 4,687,478, entitled "Shaped Sanitary Napkin With Flaps" which issued to Kees J. Van Tilburg on Aug. 18, 1987, and in U.S. Pat. No. 4,589,876, entitled "Sanitary Napkin" which issued to Kees J. Van Tilburg on May 20, 1986, the disclosures of both patents being incorporated herein by reference. It will be apparent that the polymeric compostable films described herein may be used as the liquid impervious backsheet of such sanitary napkins. On the other hand it will be understood the present invention is not limited to any specific sanitary napkin configuration or structure.

In general, sanitary napkins comprise a liquid impervious backsheet, a liquid pervious topsheet, and an absorbent core placed between the backsheet and the topsheet. The backsheet comprises one of the biodegradable multilayer films described above. The topsheet may comprise any of the topsheet materials discussed with respect to diapers.

Importantly, the absorbent articles according to the present invention are compostable to a greater extent than conventional absorbent articles which employ a polyolefin, typically a polyethylene backsheet.

The term "compostable" as used herein means a material that meets the following three requirements: (1) is capable of being processed in a composting facility for solid waste; (2) if so processed will end up in the final compost; and (3) if the compost is used in the soil the material will ultimately biodegrade in the soil.

A polymer film material present in solid waste submitted to a composting facility for processing does not necessarily end up in the final compost. Certain composting facilities subject the solid waste stream to air classification prior to further processing, in order to separate paper and other materials. A polymer film would most probably be separated from the solid waste stream in such an air classification and therefore not be processed in the composting facility. Nevertheless, it may still be a "compostable" material according to the above definition because it is "capable" of being processed in a composting facility.

The requirement that the material ends up in the final compost typically means that it undergoes a form of degradation in the composting process. Typically, the solid waste stream will be subjected to a shredding step in an early phase of the composting process. As a result, the polymer film will be present as shreds rather than a sheet. In the final phase of the composting process, the finished compost will be subjected to a screening step. Typically, the polymer shreds will not pass through the screens if they have retained the size they had immediately after the shredding step. The compostable materials of the present invention will have lost enough of their integrity during the composting process to allow semidegraded shreds to pass through the screens. However, it is conceivable that a composting facility might subject the solid waste stream to a very rigorous shredding and a rather coarse screening, in which case nondegradable polymers like polyethylene would meet requirement (2). Therefore, meeting requirement (2) is not enough for a material to be compostable within the present definition.

What does distinguish the compostable material as defined herein from materials like polyethylene is requirement (3) that they ultimately biodegrade in the soil. This biodegradation should be complete to $CO_2$ and water. This biodegradability requirement is not essential to the composting process or the use of composting soil. Solid waste and the compost resulting therefrom may contain all kinds of nonbiodegradable materials, for example, sand. However, to avoid a build up of man-made materials in the soil, it is required herein that such materials be fully biodegradable. By the same token, it is not at all necessary that this biodegradation be fast. As long as the material itself and intermediary decomposition products are not toxic or otherwise harmful to the soil or the crops, it is fully acceptable that their biodegradation takes several months or even years, since this requirement is present only to avoid an accumulation of man-made materials in the soil.

The following example illustrates the practice of the present invention but is not intended to be limiting thereof.

EXAMPLE 1: MULTILAYER FILMS

MOISTURE SENSITIVE CORE WITH THERMALLY SENSITIVE SKINS

A three layer film comprising a core layer of Vinex 2034 thermoplastic polyvinyl alcohol and two skin layers of Tone 787 polycaprolactone is prepared on a cast film coextrusion line equipped with a 6.35 cm. diameter NRM single screw extruder feeding the Vinex layer, and two 30 mm. diameter single screw satellite extruders (Zahnradwerk Kollman) feeding the two Tone 787 skin layers. All screws are standard polyolefin types. The three extruders are connected to a 60.96 cm. wide Cloeren 3 layer vane die. Cooling, slitting, and winding of the film is accommplished with a Johnson take-off system.

The temperature of the NRM extruder varies from about 177° C. at the feed zone to about 210° C. at the discharge end near the die. The adapter connecting the die to the extruder is maintained at 210° C. The temperature profiles of the two satellite extruders range from 138° C. at the feed zones to about 160° C. at their discharge ends. Both adapters connecting the satellites to the die are maintained at 160° C. The die temperature varies across its width from about 160° C. at the outer edges to about 199° C. near the center. The cooler edges help keep the film from developing edge tears as it is drawn from the die. The chill rolls on which the film is cooled and solidified are maintained at about 10° C. After cooling the thick edges of the film are slit off and removed and the final film, approximately 34.3 cm. in width, is collected on a 3 inch diameter cardboard core.

The extruder speeds and film take off speeds are adjusted to provide a film of about 0.0012 inches (30.5 microns) overall thickness. The thickness of the Vinex core layer comprises about 60 to about 70 percent of the total film thickness while the thicknesses of the two skin layers each comprise about 15 to about 20 percent of the total film thickness. The resulting film is translucent and displays excellent toughness and mechanical strength. Its properties are outlined below.

a) a machine direction (MD) tensile modulus of $1.29 \times 10^9$ dynes/sq. cm. (18,700 psi);
b) a MD tear strength of 74 grams per 25.4 microns of thickness;
c) a cross direction tear strength of 71 grams per 25.4 microns of thickness;
d) an impact strength of 107 cm.;
e) a moisture transport rate of 0.00099 grams per sq. cm. per 16 hours; and
f) a modulus at 60° C. of $7.52 \times 10^8$ dynes/sq. cm. (10,900 psi).

As can be seen, the film properties fall within the aforementioned specifications for backsheets of absorbent articles.

What is claimed is:

1. A biodegradable liquid-impervious multilayer film comprising:
   a first polymer film layer and a second polymer film layer joined to said first layer; said polymer film layers comprising a thermoplastic polymer capable of forming a film by a melt process, said thermoplastic polymer being selected from the group consisting of:
   (a) moisture sensitive polymers selected from the first group consisting of interpenetrated networks of destructurized starch, mixtures of destructurized starch, thermoplastic polyvinyl alcohol compositions, hydroxypropyl cellulose, and mixtures thereof;
   (b) thermally sensitive polymers selected from the group consisting of polycaprolactone, other aliphatic polyesters having melting points below about 65° C. or Vicat softening points of 45° C. or less, and mixtures thereof;
   (c) mechanically limited polymers selected from the group consisting of cellulose esters, cellulose ester blends with polycaprolactone, cellulose ester blends with polyhydroxybutyrate/valerate copolymers, and mixtures thereof;
   (d) poly(alpha-hydroxy alkanoates);
   (e) hydrolytically cleavable aromatic/aliphatic polyester copolymers selected from the group consisting of copolymers of polyethylene terephthalate and polybutylene terephthalate, wherein the aliphatic fraction of said copolymer is derived from the group consisting of oxalates, malonates, succinates, glutarates, adipates, pimelates, suberates, azelates, sebacates, nonanedioates, glycolates, and mixtures thereof;
   (f) oxidized ethylene/carbon monoxide copolymers;
   (g) aliphatic polyesters having melting temperatures or glass transition temperatures above 65° C.; and
   (h) thermoplastic, biodegradable elastomers selected from the group consisting of polycaprolactone/diene block copolymers and aliphatic polyester urethanes;

said first and second polymer film layers comprising different polymers;
said multilayer film having:

a machine direction (MD) tensile modulus from about $6.895 \times 10^8$ dynes/sq. cm. to $6.895 \times 10^9$ dynes/sq. cm. (10,000 to about 100,000 lbs./sq. in.);

a MD tear strength of at least 70 grams per 25.4 microns of thickness;

a cross machine direction (CD) tear strength of at least 70 grams per 25.4 microns of thickness;

an impact strength of at least 12 centimeters as measured by falling ball drop;

a moisture transpod rate less than about 0.0012 grams per square centimeter per 16 hours;

a modulus at 60° C. of at least $5.52 \times 10^7$ dynes/sq. cm. (800 lbs./sq. in.); and a thickness from about 12 microns to about 75 microns.

2. The multilayer film of claim 1 wherein said poly(alpha-hydroxy alkanoate) is selected from the group consisting of polyhydroxybutyrate, polyhydroxybutyrate/valerate copolymers, and mixtures thereof.

3. The multilayer film of claim 1 wherein said oxidized ethylene/carbon monoxide copolymer is derived from ethylene/carbon monoxide copolymers containing 0.5 to 20 weight percent carbon monoxide.

4. The multilayer film of claim 1 wherein the multilayer film additionally comprises a third polymer film layer joined to said second layer such that the multilayer film comprises a center core layer formed by said second layer positioned between two outer layers formed by said first and third layers, said third polymer film layer comprising a thermoplastic polymer capable of forming a film by a melt process, said thermoplastic polymer being selected from the group consisting of (a) moisture sensitive polymers selected from the group consisting of interpenetrated networks of destructurized starch, mixtures of destructurized starch, thermoplastic polyvinyl alcohol compositions, hydroxypropyl cellulose, and mixtures thereof;

(b) thermally sensitive polymers selected from the group consisting of polycaprolactone, other aliphatic polyesters having melting points below about 65° C. or Vicar softening points of 45° C. or less, and mixtures thereof;

(c) mechanically limited polymers selected from the group consisting of cellulose esters, cellulose ester blends with polycaprolactone, cellulose ester blends with polyhydroxybutyrate/valerate copolymers, and mixtures thereof;

(d) poly(alpha-hydroxy alkanoates);

(e) hydrolytically cleavable aromatic/aliphatic polyester copolymers selected from the group consisting of copolymers of polyethylene terephthalate and polybutylene terephthalate, wherein the aliphatic fraction of said copolymer is derived from the group consisting of oxalates, malonates, succinates, glutarates, adipates, pimelates, suberates, azelates, sebacates, nonanedioates, glycolates, and mixtures thereof;

(f) oxidized ethylene/carbon monoxide copolymers;

(g) aliphatic polyesters having melting temperatures or glass transition temperatures above 65° C.; and (h) thermoplastic, biodegradable elastomers selected from the group consisting of polycaprolactone/diene block copolymers and aliphatic polyester urethanes.

5. The multilayer film of claim 4 wherein said center core layer comprises 30 to about 80 percent of the total thickness of the multilayer film and each of said outer layers comprise 10 to 35 percent of the total thickness of the multilayer film.

6. The multilayer film of claim 5 wherein said center core layer is selected from said moisture sensitive polymers and each of said outer layers is selected from the group consisting of said thermally sensitive polymers, said mechanically limited polymers, said hydrolytically cleavable aromatic/aliphatic polyester copolymers, said oxidized ethylene/carbon monoxide copolymers, said aliphatic polyesters having melting temperatures or glass transition temperatures above 65° C., said thermoplastic, biodegradable elastomers, and mixtures thereof.

7. The multilayer film of claim 5 wherein said center core layer is selected from said thermally sensitive polymers and each of said outer layers is selected from the group consisting of said mechanically limited polymers, said hydrolytically cleavable aromatic/aliphatic polyesters, said oxidized ethylene/carbon monoxide copolymers, said aliphatic polyesters having melting temperatures or glass transition temperatures above 65° C., and mixtures thereof.

8. The multilayer film of claim 5 wherein said center core layer is a poly(alpha-hydroxy alkanoate) and each of said outer layers is selected from the group consisting of said thermally sensitive polymers, said mechanically limited polymers, said hydrolytically cleavable aromatic/aliphatic polyester copolymers, said oxidized ethylene carbon/monoxide copolymers, said aliphatic polyesters having melting temperatures or glass transition temperatures above 65° C., and mixtures thereof.

9. The multilayer film of claim 5 wherein said center core layer is selected from said thermoplastic, biodegradable elastomers and each of said outer layers is selected from the group consisting of said thermally sensitive polymers, said mechanically limited polymers, said hydrolyrically cleavable aromatic/aliphatic polyester copolymers, said oxidized ethylene/carbon monoxide copolymers, said aliphatic polyesters having melting temperatures or glass transition temperatures above 65° C., and mixtures thereof.

10. The multilayer film of claim 4 additionally comprising a biodegradable tie resin layer positioned between said center core layer and at least one of said outer layers.

11. The multilayer film of claim 10 wherein said tie resin layer is polycaprolactone.

* * * * *